United States Patent [19]

Grzybowski et al.

[11] Patent Number: 5,613,624
[45] Date of Patent: Mar. 25, 1997

[54] POWDER DISPENSER

[75] Inventors: Albert Grzybowski, Mundelein; Andrew Grzybowski, Spring Grove; Richard Rieck, Mundelein, all of Ill.

[73] Assignee: Bohdan Automation, Inc., Mundelein, Ill.

[21] Appl. No.: 488,653

[22] Filed: Jun. 8, 1995

[51] Int. Cl.$^6$ ....................................................... B67D 5/64
[52] U.S. Cl. ............................ 222/161; 222/233; 222/413
[58] Field of Search .................................... 222/161, 164, 222/167, 168, 169, 154, 196, 199, 325, 233, 239–241, 413

[56] References Cited

U.S. PATENT DOCUMENTS

| 3,377,988 | 4/1968 | Zawiski | 222/161 |
| 3,669,076 | 6/1972 | Ellis | 222/169 |
| 3,799,404 | 3/1974 | Taupin | 222/168 |
| 4,266,694 | 5/1981 | Hehl | 222/413 |
| 5,381,967 | 1/1995 | King | 222/161 |

Primary Examiner—Philippe Derakshani
Attorney, Agent, or Firm—Dorn, McEachran, Jambor & Keating

[57] ABSTRACT

A dispenser for dispensing measured amounts of powder for use in automated sample handling. The dispenser includes a cylindrical housing having a central cavity with an axial opening into the cavity at one end of the housing and a relatively narrow passage from the cavity leading out of the cylindrical housing through a nozzle at the opposite end thereof. A powder containing vial is removably mounted on the cylindrical housing. A radial passage through the cylindrical housing connects the vial with the narrow passage to discharge powder out through the nozzle. The cylindrical housing is rotatable supported on a mount through which extends a driven shaft. The driven shaft includes a worm drive located in the relatively narrow passage. A drive belt is provided to oscillate the cylindrical housing and the powder reservoir.

3 Claims, 1 Drawing Sheet

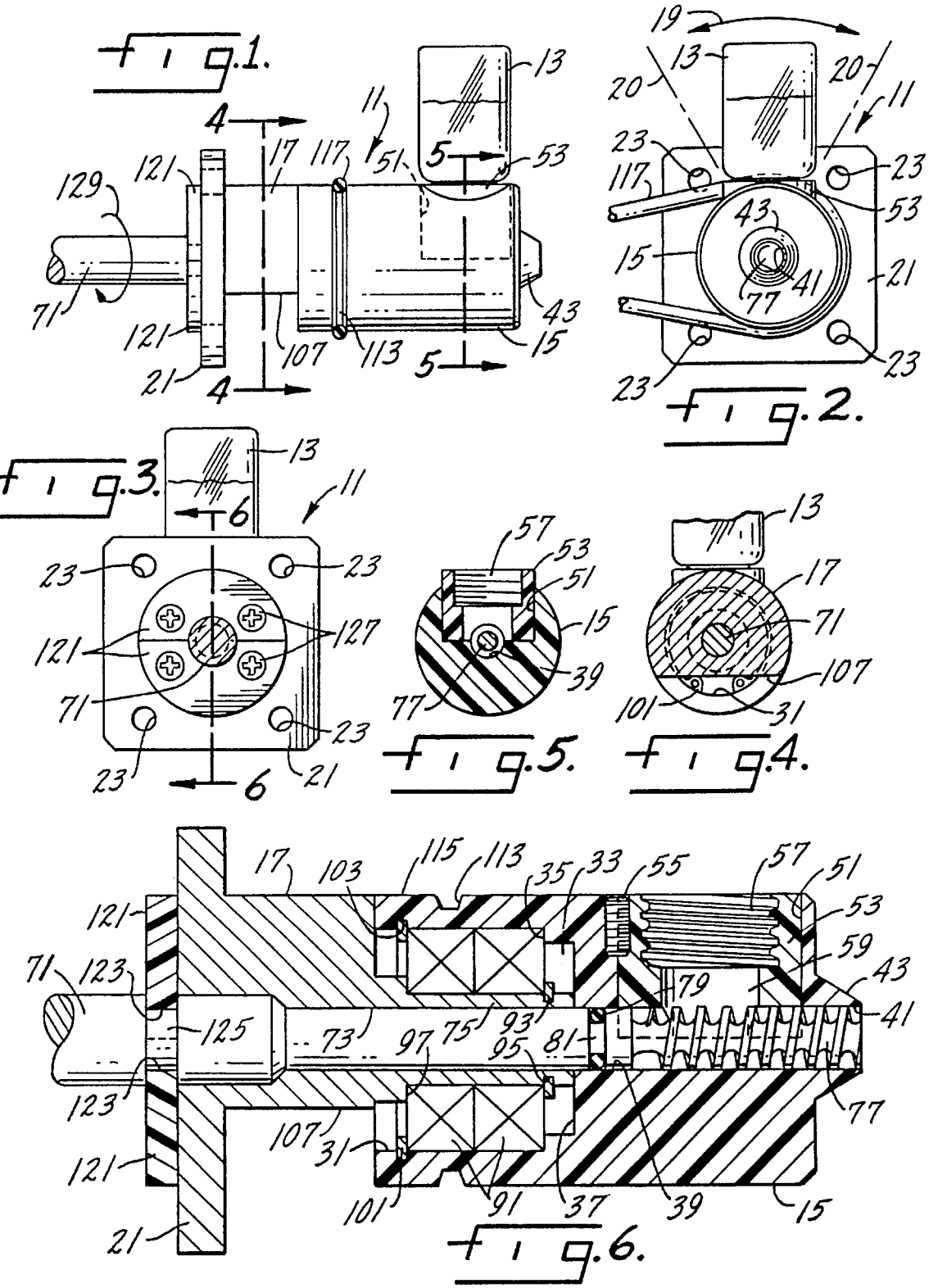

1

POWDER DISPENSER

BACKGROUND AND SUMMARY OF THE INVENTION

This invention is directed to a mechanism for precisely dispensing measured amounts of powder for use in laboratory analysis.

An object of this invention is a dispenser for powder used in automated sample handling which eliminates the problem of undersized dosages due to powder clogging or caking in the dispensing mechanism.

Another object of this invention is a powder dispenser having a worm drive that can be driven continuously or intermittently depending on need.

Another object of this invention is a dispenser for powder in which the interruption of the powder flow to the dispenser worm drive because of caking or clogging of the powder is prevented by oscillating the dispenser housing.

Another object of this invention is a dispenser for powder which securely mounts on a drive shaft support bracket and can be easily disassembled for cleaning.

Another object of this invention is a dispenser for powder which may be operated automatically as a component of an automated work station.

Another object of this invention is a dispenser which may be manually operated.

Other objects may be found in the following specification, claims and drawings.

BRIEF DESCRIPTION OF THE DRAWINGS

The invention is illustrated more or less diagrammatically in the following drawings wherein:

FIG. 1 is a side elevational view of the dispenser of this invention with some parts shown in hidden lines and others broken away;

FIG. 2 is an end elevational view of the dispenser of FIG. 1 with the center lines of the rotated positions of the dispenser shown by phantom lines;

FIG. 3 is an opposite end view of the dispenser of FIG. 2;

FIG. 4 is a cross sectional view taken along line 4—4 of FIG. 1;

FIG. 5 is a cross sectional view taken along line 5—5 of FIG. 1 with the powder vial omitted for clarity of illustration; and FIG. 6 is an enlarged cross sectional view taken along line 6—6 of FIG. 3.

DESCRIPTION OF THE PREFERRED EMBODIMENT

The powder dispenser 11 of this invention includes a powder reservoir which may be a small glass bottle or vial 13 removably supported on a cylindrical housing 15. The cylindrical housing 15 is rotatably supported on a mount 17 for oscillating movement as shown by the arrow 19 in FIG. 2 of the drawings between center line positions indicated by the phantom lines 20. The housing mount 17 has an integrally formed rectangular plate 21 with bolt holes 23 near the corners thereof for attaching the mount to a support or a machine which is not shown in the drawings.

A large axial opening 31 is formed in the longitudinal end of the cylindrical housing 15 adjacent the mount 17. This axial opening leads into a central cavity 33 of the cylindrical housing. A shoulder 35 is formed in the central cavity slightly axially outwardly of the end wall 37 of the cavity. A narrow cylindrical passage 39 extends from the end wall 37 of the cavity through a discharge opening 41 located in the opposite longitudinal end of the cylindrical housing which discharge opening is surrounded by a nozzle 43.

A radial socket opening 51 is formed in the cylindrical housing 15 near the nozzle 43 and extends into the narrow cylindrical passage 39. A tubular collar 53, which forms a support for the powder reservoir vial 13, is seated in the radial socket opening 51 and held thereto by a set screw 55. The tubular collar has interior threads 57 which receive corresponding threads of the powder reservoir vial 13, which threads are not shown in the drawings. The tubular collar 53 also defines a cylindrical passage 59 leading from the radial socket opening 51 into the narrow cylindrical passage 39.

A drive shaft 71, which is driven by an external source of power, either mechanical, electrical or manual, extends through a passage 73 in the mount 17, through a sleeve 75 formed integrally with the mount 17 and into the narrow cylindrical passage 39 where the drive shaft is shaped as a worm thread 77. An O-ring 79 seats in an annular groove 81 formed in the drive shaft to form a seal between the drive shaft and the worm thread 77 to prevent the seepage of powder.

To provide for ease of rotational movement of the cylindrical housing 15 relative to the mount 17, ball bearings 91 are mounted on the sleeve 75 inside the central cavity 33 of the cylindrical housing and in engagement with inner surface of the cylindrical housing. The ball bearings are held in position relative to the sleeve 75 by a lock ring 93 which seats in a groove 95 formed in the sleeve 75. The ball bearings 91 are held between the lock ring 93 and a shoulder 97 formed at the end of the sleeve.

In order to removably attach the cylindrical housing 15 to the mount 17, a lock ring 101 is provided which fits in a groove 103 formed in the inner surface of the cylindrical housing 15 inside the central cavity 33. The lock ring 101 engages the radial outer end of the ball bearings 91 to secure them between the lock ring 93 and the shoulder 35 of the central cavity.

Access to the lock ring 101 for removal and reinstallation of the cylindrical housing 15 relative to the mount 17 is provided by a notch 107 in the mount 17. The notch 107 provides access to the central cavity 33 through the axial opening 31 at a longitudinal end of the cylindrical housing 15. To allow oscillation of the cylindrical housing 15 relative to the mount 17 in the directions shown by the arrow 19 in FIG. 2, an outwardly opening groove 113 is formed in the outer wall 115 of the cylindrical housing 15. A drive belt 117 seats in this groove and is moved by a drive which is not shown. The engagement of the drive belt with the groove 113 will also help maintain the cylindrical housing 15 in its at rest position shown in FIG. 3 of the drawings.

The drive shaft 71 is held secured to the mount 17 by semi-circular plates 121 having notches 123 which seat in a groove 125 formed in the shaft 71. The plates are held in position by screws 127.

Rotation of the shaft 71 in the direction shown by the arrow 129 in FIG. 1 rotates the worm thread 77 to move the powder out through the discharge opening 41 in the nozzle 43. The number of rotations of the worm thread can be controlled to charge a precise amount of powder through the discharge opening 41 and into a suitable receptacle, which is not shown. The supply of powder can be replenished by replacement of the vial which forms the powder reservoir 13. The vial can be threadably removable from the threads 57 of the tubular collar mount 53. To prevent the powder in the reservoir 13 or in the passage 59 in the mount 53 of the bottle from clogging or caking, the cylindrical housing 15 may be oscillated back and forth in the directions indicated by the arrow 19 in FIG. 2 by reciprocal movement of the drive belt 17 which fits in the groove 113 in the outer surface 115 of the cylindrical housing 15. This oscillation may be controlled by a suitable drive timed in accordance with the characteristics of the powder to avoid caking or clogging.

When it is desirable to disassemble the cylindrical housing 15 for cleaning or other maintenance, the lock ring 101 can be removed from the groove 103 to permit removal of the cylindrical housing relative to the mount and its ball bearings 91 simply by accessing the lock ring 101 through the axial opening 31 in the cylindrical housing 15 which is accessible adjacent the cut away portion 107 of the mount 15.

We claim:

1. A dispenser for dispensing measured amounts of powder for use in automated sample handling, said dispenser including:

a cylindrical housing having an axial opening at one longitudinal end leading into a central cavity, a relatively narrow passage extending from said central cavity and exiting axially through a smaller axial opening in the other longitudinal end of said cylindrical housing, a cylindrical passage extending through said cylindrical housing and communicating with said relatively narrow passage, a tubular collar installed in said cylindrical passage, a mount supporting said cylindrical housing for rotation relative thereto, a driven shaft extending through said mount and said central cavity, a worm drive formed as part of said shaft and journalled in said relatively narrow passage to discharge powder from said powder container through said smaller axial opening, and means to oscillate said cylindrical housing relative to said mount.

2. The dispenser of claim 1 in which said means to oscillate said cylindrical housing relative to said mount includes a circumferential groove formed in said cylindrical housing and opening outwardly thereof and a drive belt seated in said groove.

3. The dispenser of claim 1 in which said cylindrical housing is affixed to said mount by a lock ring which lock ring is accessible for removal through said axial opening in said cylindrical housing.

* * * * *

UNITED STATES PATENT AND TRADEMARK OFFICE
Certificate

Patent No. 5,613,624                                                    Patented: March 25, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Albert Grzybowski, Mundelein, IL; Andrew Grzybowski, Spring Grove, IL; Richard Rieck, Mundelein, IL; Tadeusz J. Wozny, Mundelein, IL.

Signed and Sealed this Ninth Day of May, 2000.

KEVIN P. SHAVER
*Supervisory Patent Examiner*
Art Unit 3754